(12) United States Patent
McDonald

(10) Patent No.: US 10,625,001 B2
(45) Date of Patent: Apr. 21, 2020

(54) CHEST SEAL AND VACUUM SYSTEM

(71) Applicant: Rex McDonald, London, KY (US)

(72) Inventor: Rex McDonald, London, KY (US)

( * ) Notice: Subject to any disclaimer, the term of this patent is extended or adjusted under 35 U.S.C. 154(b) by 578 days.

(21) Appl. No.: 15/731,125

(22) Filed: Apr. 24, 2017

(65) Prior Publication Data

US 2017/0312402 A1 Nov. 2, 2017

Related U.S. Application Data

(60) Provisional application No. 62/391,511, filed on May 2, 2016.

(51) Int. Cl.
| | | |
|---|---|---|
| *A61M 1/00* | (2006.01) | |
| *A61M 1/04* | (2006.01) | |
| *A61F 13/00* | (2006.01) | |
| *A61F 13/14* | (2006.01) | |
| *A61F 13/02* | (2006.01) | |

(52) U.S. Cl.
CPC ..... *A61M 1/0031* (2013.01); *A61F 13/00068* (2013.01); *A61F 13/0206* (2013.01); *A61F 13/0216* (2013.01); *A61F 13/143* (2013.01); *A61M 1/04* (2013.01); *A61M 2210/101* (2013.01)

(58) Field of Classification Search
CPC .................. A61M 1/0031; A61M 1/04; A61M 2210/101; A61F 13/00068; A61F 13/0206; A61F 13/0216; A61F 13/143
USPC ........................................................ 604/317
See application file for complete search history.

(56) References Cited

U.S. PATENT DOCUMENTS

| | | | |
|---|---|---|---|
| 4,465,062 A | | 8/1984 | Versaggi et al. |
| 4,717,382 A | | 1/1988 | Clemens et al. |
| 5,437,651 A | * | 8/1995 | Todd .................. A61M 1/0088 15/420 |
| 5,478,333 A | | 12/1995 | Asherman |
| 5,492,535 A | | 2/1996 | Reed et al. |
| 7,195,624 B2 | | 3/2007 | Lockwood et al. |
| 7,533,696 B2 | | 5/2009 | Paul, Jr. |
| 7,615,674 B2 | | 11/2009 | Asherman |
| 7,834,231 B2 | | 11/2010 | Biddle et al. |
| 8,758,305 B2 | | 6/2014 | Memahon |
| 2008/0091152 A1 | * | 4/2008 | Asherman ............... A61M 1/04 604/315 |
| 2010/0004599 A1 | | 1/2010 | Zhou et al. |
| 2010/0032386 A1 | | 2/2010 | Lehovec |

(Continued)

*Primary Examiner* — Andrew J Mensh

(57) ABSTRACT

A chest wound seal for treating traumatic pneumothorax following a penetrating chest wound. The chest wound seal comprises a wound pad with an absorbent bottom surface and a nonporous top surface embedded with unidirectional valves that allow evacuation of air and fluid from the pleural cavity but prevents re-entry of air into the thorax. A central vacuum column mounted over at least one unidirectional valve. The chest wound seal further comprises a plurality of wound pad segments radiating from the central vacuum column, wherein each segment comprises at least one manual valve configured to create a separate sealed area against the skin surface to suit body types with different size and morphological features. The central vacuum column is adapted to be connected to a vacuum pump which enables evacuation of harmful air and fluid from the pleural cavity thereby reducing the shock induced by hypoxia and increasing patient survivability.

20 Claims, 20 Drawing Sheets

(56) References Cited

U.S. PATENT DOCUMENTS

| | | |
|---|---|---|
| 2012/0046582 A1 | 2/2012 | Hopman et al. |
| 2012/0281933 A1 | 11/2012 | Beer |
| 2014/0188090 A1* | 7/2014 | Riesinger .............. A61F 13/066 |
| | | 604/543 |
| 2016/0120706 A1* | 5/2016 | Collinson ........... A61F 13/0253 |
| | | 604/319 |
| 2016/0193394 A1* | 7/2016 | Simmons .......... A61F 13/00068 |
| | | 604/319 |

* cited by examiner

CHEST SEAL AND VACUUM SYSTEM

CROSS REFERENCE TO RELATED APPLICATIONS

This application claims the benefit of priority to U.S. provisional application Ser. No. 62/391,511 filed on 2 May 2016, hereby incorporated by reference in its entirety.

BACKGROUND

1. Field of the Invention

The present invention generally relates to medical devices and systems for treating open chest wounds. More specifically, this invention relates to a chest wound seal and an integrated vacuum pump device adaptable to different body types for treatment of traumatic pneumothorax without increasing the pain of the wounded victim.

2. Description of Related Arts

Thoracic injuries account for a majority of all deaths resulting from traumatic injury. Penetrating chest injuries occur largely due to a gunshot, stabbing or whenever an object punctures the chest wall forming an open chest wound which permits air to enter into the chest cavity of the wounded victim during inhalation. When air enters the pleural space, the normal vacuum that occurs with the expansion of the ribs through muscular action cannot occur. As each lung is contained within a separate pleura, a penetration to one side of the chest wall forms a positive intrapleural pressure resulting in deflation of lung on the injured side due to the accumulation of harmful air or liquid within the pleural cavity. The deflated lung loses the ability to expand and absorb oxygen thus resulting in a lack of oxygen in the blood further leading to loss of consciousness and coma. Lack of sufficient amount of oxygenated blood causes the body to go into shock and may also result in death.

Open chest wound must be sealed immediately in order to prevent air from entering the chest cavity and collapsing the lung. In battlefield conditions, the penetrating chest wound must remain sealed till the casualty is evacuated and transferred to a medical treatment facility. Since most dressings and bandages allow air to pass through, the open chest wound must be first sealed with a non-porous, airtight material to block the entry of air into the chest cavity. Even with the use of airtight chest sealing material, there are still chances for developing tension pneumothorax due to the air or fluid accumulated within the chest cavity resulting in a positive intrathoracic pressure. Therefore, the positive intrathoracic pressure needs to be released in order to re-inflate the collapsed lung. Evacuation of harmful air or liquid accumulated within the pleural cavity allows re-inflation of collapsed lung.

Different types of wound sealing devices have been developed to seal open chest wounds or penetrating thoracic wounds. Advancement in the field of disposable medical devices led to the development of sterile occlusive dressings for creating an airtight seal over the wounded thorax region. The occlusive dressing further consists of one or more one-way valves which selectively allows exit of unwanted air or liquid from the chest cavity but prevents any ingress of air or liquid. However, these existing disposable occlusive dressings are generally available in standard measurements mostly covering a single open chest wound and require the application of excessive manual pressure over the wounded site in order to form a tight seal which further increases the pain of the wounded subject.

From the prior art, U.S. Pat. No. 7,834,231 B2 to Biddle discloses a low-profile chest seal for treating an open pneumothorax. The chest seal comprises a flange body with an adhesive layer disposed on the bottom surface for adhering to the skin's surface and one-way valves secured to the upper surface which allows air to escape from a chest wound and precludes airflow into the chest wound. However, the application of this chest seal was restricted to the treatment of limited types of penetrating chest wounds, especially gunshot wounds caused by penetration of a bullet entering directly from the front side or from the back side of the chest. It makes no accommodation for wounds that enter from the side, mammary region or adipose tissue on the chest. The chest seal of Biddle has no flexibility for adapting to different body types, especially the body types that was not set forth in the 1957 guideline for a 145-pound male soldier. For example, the chest seal of Biddle would be ineffective to accommodate a woman's body morphology or to adapt to body types of a civilian population with varying body fat indexes. Using the chest seal of Biddle, there is no active way to improved oxygenation to a traumatized victim.

U.S. Pat. No. 7,615,674 B2 to Asherman discloses a chest dressing assembly with a rigid body comprising an inner chamber and one or more check valves on the rigid body that allow fluid to flow out of the chamber but prevent re-entry of fluid into the chamber. However, the chest dressing of Asherman involves a pumping action, wherein the force is applied directly at the point of injury which may further cause damage to the wound and makes self-use of the dressing impossible by the wounded victim.

US patent publication 20120046582 A1 to Hopman discloses a medical chest seal comprising a one-way valve and a closure member for selectively covering a portion of the valve thus protecting against the intrusion of contaminants and prevents fluid flow. However, none of the prior arts addresses the problem of adaptability of the chest wound seal to different human and animal body types while maintaining an airtight seal against the skin surface. In addition, the time required for deployment of the seal and complexity of operation further delays the process of relieving pneumothorax.

U.S. Pat. No. 8,758,305 B2 to Mcmahon discloses a low-pressure check one-way valve, for use in medical technique. The valve consisting of an inlet half and an outlet half and having an inlet channel and an outlet channel with a diaphragm being positioned in a pressure space consisting two pressure chambers contacting an annular valve seat under pre-tension which is opening into the outlet channel. In the direction of flow before the closing mechanism formed by the valve seat and the diaphragm, a second valve mechanism is provided which is opening in the same sense with the first closing mechanism at an over-pressure in the entry channel and which is closing at an over-pressure in the exit channel.

US patent publication 20120281933 A1 to Beer discloses a one-way valve for use in flexible packages. The valve comprises a flexible base layer, a flexible cover layer and an interposed layer of oil. The cover layer is secured to the base layer along respective contiguous portions of side edges to form an openable channel. The oil layer is located in the channel between the base layer and the cover layer and over the hole to form a bond holding the cover layer on the base layer until the pressure within the package causes the bond to break, whereupon the cover layer to lift ups and opens the hole valve.

US patent publication 20100032386 A1 to Lehovec discloses a purification process of a contaminated liquid by distillation in which the temperature difference is generated by a Peltier heat pump inserted between the condensed purified liquid and the contaminated liquid. The air space between the contaminated liquid and the distilled purified liquid is evacuated by the use of a manually operated vacuum pump, which creates a vacuum in a cylinder by moving a piston in the cylinder, sucking in air from the chamber to be evacuated into said vacuum and then expelling the sucked-in air from the cylinder into the ambient by reversing the motion of the piston.

US patent publication 2010004599 A1 to Zhou et al., discloses a one-way valve for a trocar. The valve comprises a V-shaped funnel acting as the upper portion of the one-way valve, a slit cut into the bottom surface of the V-shaped funnel and a supporting body acting as the lower portion of the one-way valve and providing the additional sealing pressure to the slit. The supporting body is connected to the outside of the inclined plane of the V-shaped funnel construction.

U.S. Pat. No. 7,533,696 B2 to Paul, Jr., discloses a one-way valve apparatus for use in draining fluid from a patient. The valve has an inlet end, an outlet end and a fluid pathway extending therebetween. The valve inlet end is engaged with the housing inlet end to comprise an open valve inlet end for receiving the fluid to be drained. The valve outlet end is in a normally closed position and is adapted to partially open to permit drainage of fluid received through the pathway from the inlet end and to return to the normally closed position upon drainage of the fluid.

U.S. Pat. No. 7,195,624 B2 to Lockwood et al., discloses a ventilated bandage system for use with a wound. The bandage is connectable to a vacuum source for creating a negative pressure between the bandage and the wound. The bandage comprises discrete passageways in communication with wound surface and the vacuum source and a vent in communication with the atmosphere surrounding the bandage.

U.S. Pat. No. 5,492,535 to Reed et al., discloses a manually operated pumping apparatus for use in catheterization procedures. The apparatus comprises two pumps supported in a housing in a parallel arrangement. The pumps are engaged by a rack and pinion actuating assembly which provides reciprocating linear movement to the two pumps during operation so that one pump performs a pumping stroke while the other pump simultaneously performs a suction stroke. The actuating assembly is driven by a drive assembly which converts rotation of a handle into linear motion usable by the rack and pinion members to drive the two pumps in their reciprocating pumping movements.

U.S. Pat. No. 5,478,333 to Asherman discloses a medical dressing for treating open chest injuries. The medical dressing of Asherman comprises a one-way air valve attached to a body attaching means with a central opening and an adhesive underside. The center of the body attaching means translates into a cylindrical duct segment that is positioned over the wound hole so that the air expelled from the wound hole passes through the duct segment and exits through the one-way valve. However, the medical dressing of Asherman fails to address the problem of adaptability of the medical dressing to different human and animal body types while maintaining an airtight seal against the skin surface.

U.S. Pat. No. 4,717,382 to Clemens et al., discloses a noninvasive apparatus for temporarily assisting in the treatment of a sucking chest wound. The apparatus comprises a dome-shaped element with a one-way valve positioned over the chest wound and strapped in a fluid tight relationship with the patient's body. However, the rigid design of the apparatus does not allow the apparatus to be used for sealing multiple wounds on a patient's body.

U.S. Pat. No. 4,465,062 to Versaggi et al., discloses a noninvasive seal for a sucking chest wound. The seal comprises a base provided with a cap which encloses a one-way check valve for preventing air from being collected and trapped in the chest cavity. The one-way check valve allows escape of air upon forceful expiration and prevents the entry of air into the chest cavity associated with a sucking chest wound. However, the noninvasive seal of Versaggi cannot be used for sealing open chest wounds of victims with different body types and morphological features.

Another limitation with existing chest wound sealing devices is that the wound sealing devices are mostly restricted to application in humans and are not possible to adapt for use in veterinary situations. There is a need for a thoracic wound seal device for sealing penetrating wounds in animals, such as when a horse have been impaled by a fencing pole or any sharp object during a storm or when a dog have been shot or impaled by an arrow during hunting.

Therefore, there still exists a need for an improved chest wound seal device accommodating different human body types and easily adaptable for treating animals with penetrating thoracic wounds. There is also a need for an easily deployable chest wound seal device that allows rapid evacuation of harmful fluid from pleural cavity thereby increasing the survivability of traumatic pneumothorax patients.

SUMMARY OF THE INVENTION

The invention primarily relates to a chest wound seal and pump device for treating traumatic pneumothorax following a penetrating chest wound. In an embodiment, the present invention relates to a unisex multi-morphology traumatic pneumothorax chest seal with an integrated vacuum pump system. The chest wound seal and pump device is adaptable for treating both male and female subjects belonging to different age groups, with varied body types and morphological features. The chest wound seal device comprises a wound pad with a plurality of segments and different types of closable valves. This unique design allows coverage of multiple wounds resulting from multiple projectiles while being highly customizable to different situations. The integrated vacuum pump system is configured for rapid deployment and efficient evacuation of harmful fluid or gas from the pleural cavity thereby reducing the shock induced by hypoxia and increasing patient survivability.

According to one embodiment, the present invention relates to a chest wound seal comprising a wound pad for sealing a penetrating thoracic wound. The wound pad of the present invention comprises a top surface comprising a nonporous layer and a bottom surface comprising an absorbent layer. A plurality of unidirectional valves embedded on the top surface enable evacuation of air or liquid from a pleural cavity and prevents the air or liquid from re-entering the thorax of the wounded victim. The wound pad further comprises a central vacuum column mounted directly over at least one unidirectional valve, wherein the central vacuum column is adapted to be connected to a vacuum pump for rapid evacuation of air or liquid from the pleural cavity. A plurality of wound pad segments radiating from the central vacuum column, the plurality of wound pad segments is demarcated from each other by perforated lines between airtight walls which allow each wound pad segment to form a separate sealing area. The wound pad, when attached to a body of a victim, is configured to seal one or more wounds by the plurality of wound pad segments. The wound pad is customizable by folding out one or more of the plurality of wound pad segments in order to suit wounded victims with different body types and morphological features. The bottom surface of the wound pad comprises an adhesive strip for attaching to a skin surface of the wounded victim and a plurality of air channels on the absorbent layer which allow evacuation of air from multiple wounds. The vacuum pump connected to the wound pad, upon actuation creates a vacuum to draw the accumulated harmful air or liquid from the pleural cavity, wherein the vacuum pump enables application of only minimal force to the wound region thereby eliminating the need to apply any increased pressure over the wound pad. The chest wound seal further comprises a flexible extension tube connected to the wound pad in a direction opposite to the vacuum column and a strap to secure the wound pad to the body of the victim when necessary. While using the flexible extension tube, all of the wound pad segments are folded up in such a way that the adhesive strip of the segments are made to adhere to the base of the vacuum pump.

According to another embodiment, the invention relates to a thoracic wound sealing device comprising a wound pad adapted to cover a wound in a thorax region of a victim. The thoracic wound sealing device comprises at least one unidirectional valve embedded within the wound pad to enable evacuation of air from a pleural cavity and prevent the air from re-entering the thorax of the victim. A vacuum column mounted directly over at least one unidirectional valve and a plurality of wound pad segments radiating from the vacuum column, wherein each of the plurality of wound pad segments is separable by tearing along the perforated line disposed between airtight walls configured to form separate sealing areas. The thoracic wound sealing device further comprises a vacuum pump connected to the wound pad through the vacuum column. Upon connecting to the vacuum column, the vacuum pump creates a vacuum to draw air or liquid from the pleural cavity. The vacuum pump enables application of normal force to the wound thus preventing from the excess force being applied to the wound.

In one aspect, the invention relates to a field deployable traumatic pneumothorax device that is adaptable to wounded victims of different body types having gender, age, and weight based differences. The device has a unique ability to cover multiple wound entry points on a victim. The device seals the chest cavity of the wounded victim while providing a low-intensity vacuum to evacuate abnormal air from the pleural cavity. The device is capable of easy deployment and operation by the victim themselves as well as by first responders. The device is configured to assist in inflation of a collapsed lung following a traumatic pneumothorax under field conditions and during transportation to a fully capable medical facility thus extending the timeline of survivability after injury. A veterinary adapter allows the device to be used in an animal care environment for the treatment of a similar type of traumatic injury in animals.

In another aspect, the invention relates to a method for treating a thoracic wound. The method comprising the steps of: i) securing a wound pad to a victim's skin to cover a wound in a thorax of a victim, wherein the wound pad comprises: a) at least one unidirectional valve embedded in the covering pad to enable evacuation of air from a pleural cavity and to prevent the air from re-entering the thorax; b) a vacuum column mounted directly over at least one unidirectional valve; c) a plurality of wound pad segments radiating from the vacuum column, wherein each of the plurality of wound pad segments are separated by a perforated line on the wound pad between airtight walls to form separate sealed areas; ii) connecting a vacuum pump to the wound pad through the vacuum column to form an airtight seal, wherein the vacuum pump comprises a handle; and iii) compressing the handle to apply force in a direction normal to the wound to create a vacuum, wherein the vacuum so created expels fluids from a pleural cavity of the victim.

BRIEF DESCRIPTION OF SEVERAL DRAWINGS

DETAILED DESCRIPTION OF DIFFERENT EMBODIMENTS

The following detailed description of the preferred embodiments presents a description of certain specific embodiments to assist in understanding the claims. However, the present invention is intended to cover alternatives, modifications, and equivalents, which may be included within the spirit and scope of the invention as defined by the appended claims. Furthermore, in the following detailed description of the present invention, numerous specific details are set forth in order to provide a thorough understanding of the present invention. However, it will be evident to one of ordinary skill in the art that the present invention may be practiced without these specific details.

Figure 1:
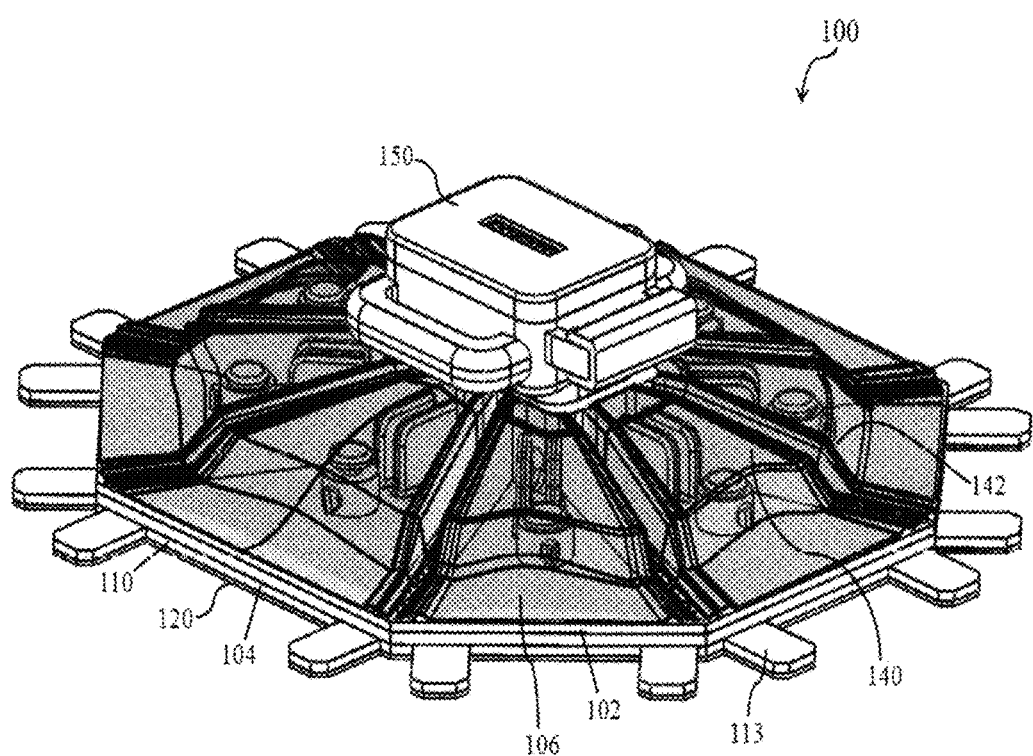
FIG. 1 is a perspective view of a chest wound seal device according to an embodiment of the invention.
Figure 2:
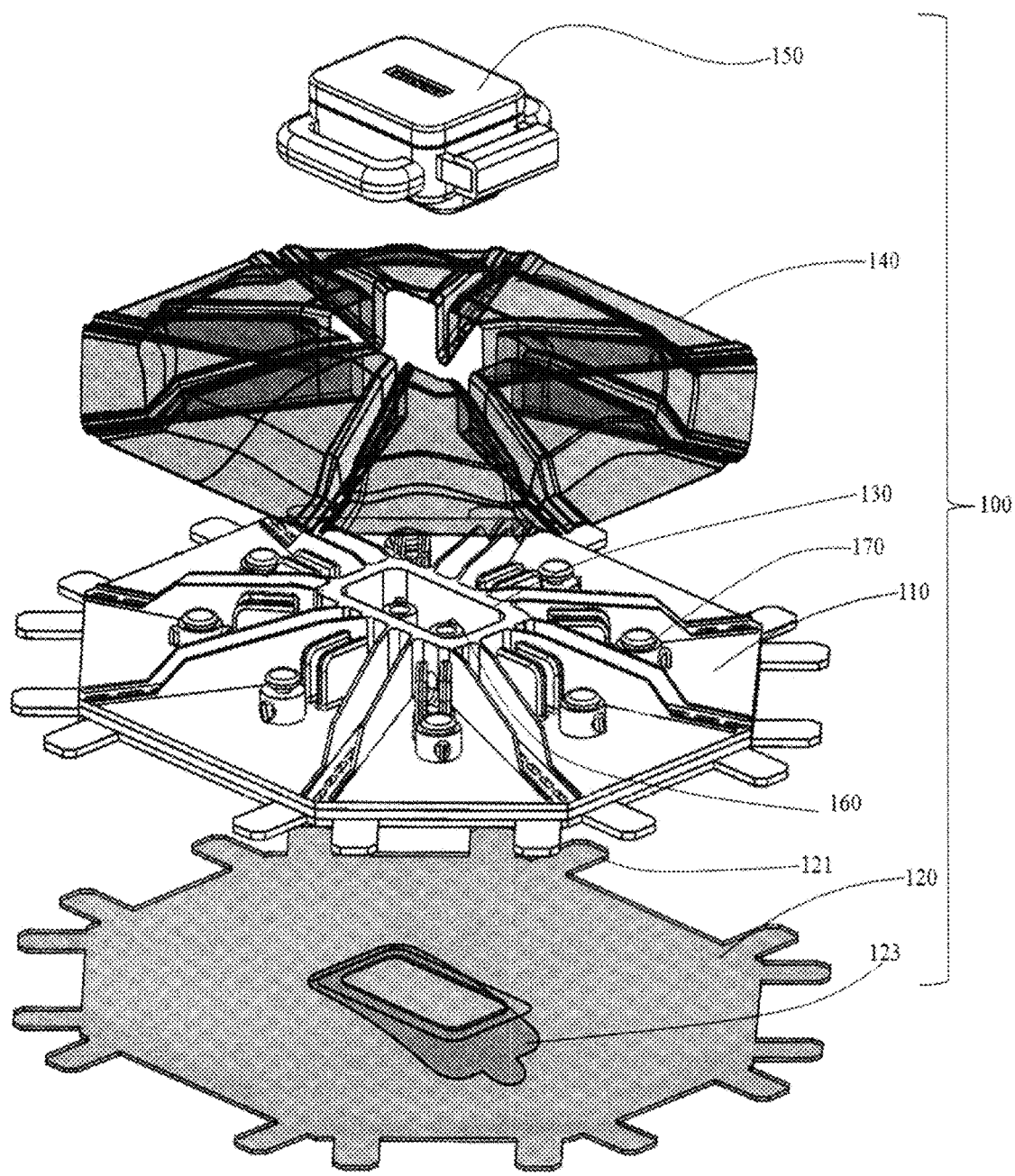
FIG. 2 is an exploded view of the chest wound seal device.

Referring to FIGS. 1 and 2 illustrating perspective and exploded views of the chest wound seal device respectively, the chest wound seal device 100 of the present invention comprises a wound pad 110 with a top surface 102 comprising a nonporous layer and a bottom surface 104 comprising an absorbent layer and a plurality of unidirectional valves 160 embedded on the top surface 102. In an exemplary embodiment, the top surface 102 comprises a plastic sheet and the bottom surface comprises a porous absorbent sheet configured to absorb fluid such as sweat and blood from the wound surface. A central vacuum column 130 is mounted over at least one unidirectional valve 160 present on the wound pad 110. The bottom surface 104 of the wound pad 110 is enclosed by a protective cover 120, which is removable using peel-off tabs 121 prior to the application of the wound pad 110 over an open chest wound. In an embodiment, the protective cover 120 is a peel off member adhering to the bottom surface 104 of the wound pad. The peel-off member 120 protects the bottom surface 104 from external contaminants thereby maintaining the wound pad 110 in a sterile condition. The protective cover 120 further comprises a flap 123 which is removable independent of the protective cover 120, especially when using a veterinary adaptor mount for adapting the device 100 to treat an animal with a penetrating wound.

One of the key features of the chest wound seal device 100 is that the wound pad 110 comprises a plurality of segments 106 at least partially separable from each other using tear tabs 113 in order to adapt to both male and female subjects with different body types and morphological features. In one embodiment, the wound pad 110 is octagon shaped and comprises multiple segments 106 radiating from the central vacuum column 130 thus forming a plurality of sectors. When the plurality of sectors of the wound pad 110 is separated from each other, the inner edge of the sectors remains attached to the central vacuum column 130. The chest wound seal device 100 further comprises a vacuum dome 140 covering the plurality of wound pad segments 106. In an embodiment, the vacuum dome 140 comprises multiple segments 142, which along with the segments 106 of the wound pad 110 constitute separate sealing units configured to seal multiple chest wounds. The device 100 further comprises an integrated vacuum pump 150 operatively connected to the central vacuum column 130 configured for rapid evacuation of air or liquid from the pleural cavity of a wounded victim. In an exemplary embodiment, the wound pad is customizable to suit a body of a wounded female victim by folding up one or more of the wound pad segments 106 out of the way of the mammary gland. One or more of the wound pad segments 106 can be lifted and folded out in such a way that the adhesive strip of segments 106 adheres to the base of the vacuum pump 150.

Figure 3:
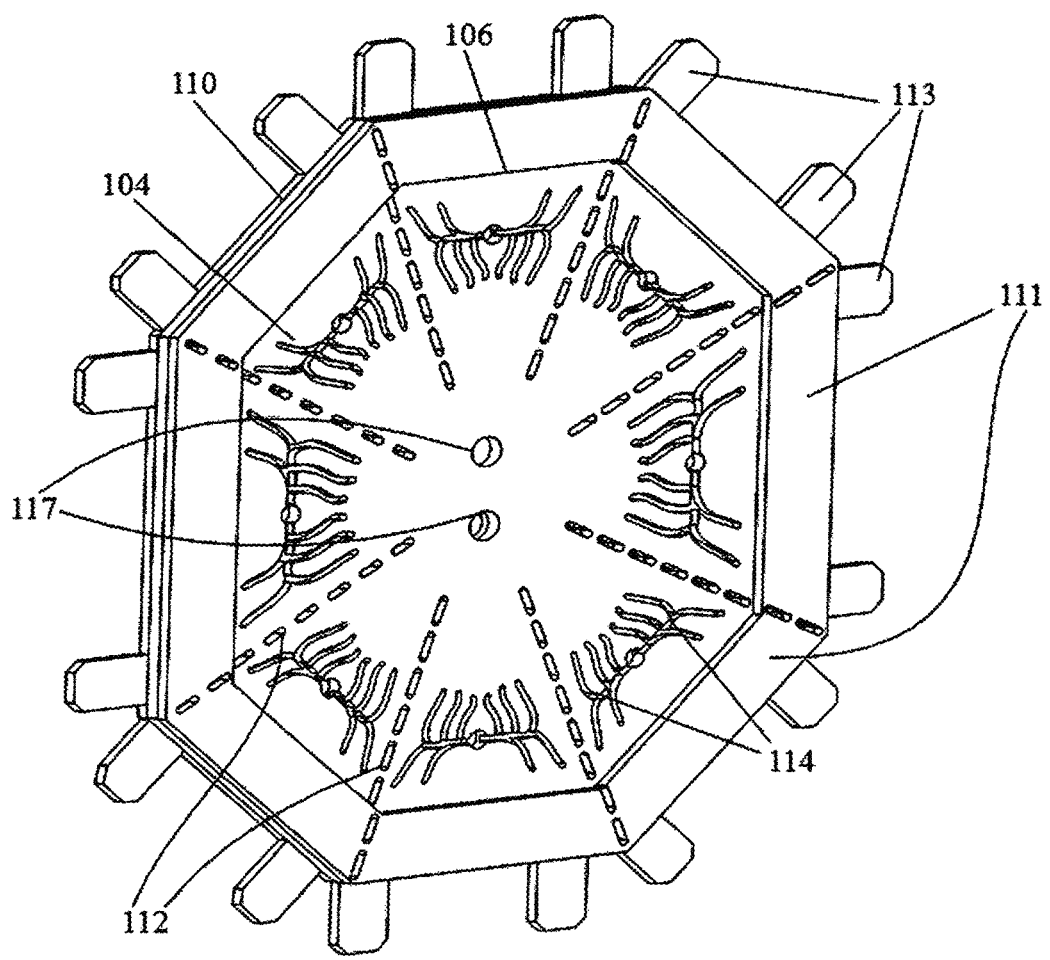
FIG. 3 is a bottom plan view of the wound pad without the protective layer.

Referring to FIG. 3, the bottom surface 104 of the wound pad 110 comprises an adhesive layer 111 disposed along the edges of the bottom surface 104 in the form of an adhesive strip, for attaching to a chest skin surface of a wounded victim to provide an airtight seal between the wound pad 110 and the skin. In one embodiment, the adhesive strip 111 is attached to an underside of the wound pad 110, such that the adhesive strip 111 surrounds the periphery of the absorbent layer at the bottom surface 104. The segments 106 of the wound pad 110 are demarcated from each other by perforated lines 112 which also extend over the adhesive layer 111 at the bottom surface 104. Each of the plurality of wound pad segments 106 comprises at least one tear tab 113 extending from an outer edge which allows easy separation of the segments 106. For example, by pulling the tear tab 113 and tearing along the perforated lines 112, one or more wound pad segments 106 can be folded out in order to customize the wound pad according to body morphology of the wounded victim. The bottom surface 104 of wound pad 110 comprises at least one central opening 117 configured to connect to at least one unidirectional valve which allow evacuation of air or fluid accumulated in the pleural cavity. Each of the plurality of wound pad segments 106 further comprises numerous air channels 114 disposed on the absorbent layer at the bottom surface 104, wherein the air channels 114 allow evacuation of air from multiple open chest wounds.

In one embodiment, the wound pad 110 comprises an octagon patterned adhesive strip 111 attached around the edges of the absorbent layer at the bottom surface 104. When applied over the open chest wound, the adhesive strip 111 sticks to the skin surface and provides an air tight seal between the wound pad 110 and the skin surface of the chest region of the wounded victim. The absorbent layer at the bottom surface 104 is configured to absorb fluids such as blood and sweat from the wound surface. The adhesive present in the adhesive strip 111 is formulated to reduce skin irritation while providing an air-tight barrier. In an exemplary embodiment, the adhesive is a non-toxic elastomer with a low probability of causing an allergic reaction. In another embodiment, the adhesive layer is made of a bio-compatible material. The adhesive is selected based on the properties such as the adhesive does not migrate in a low-pressure environment and should be able to easily peeled off from the skin causing only minimal discomfort to the wounded victim.

Figure 4:
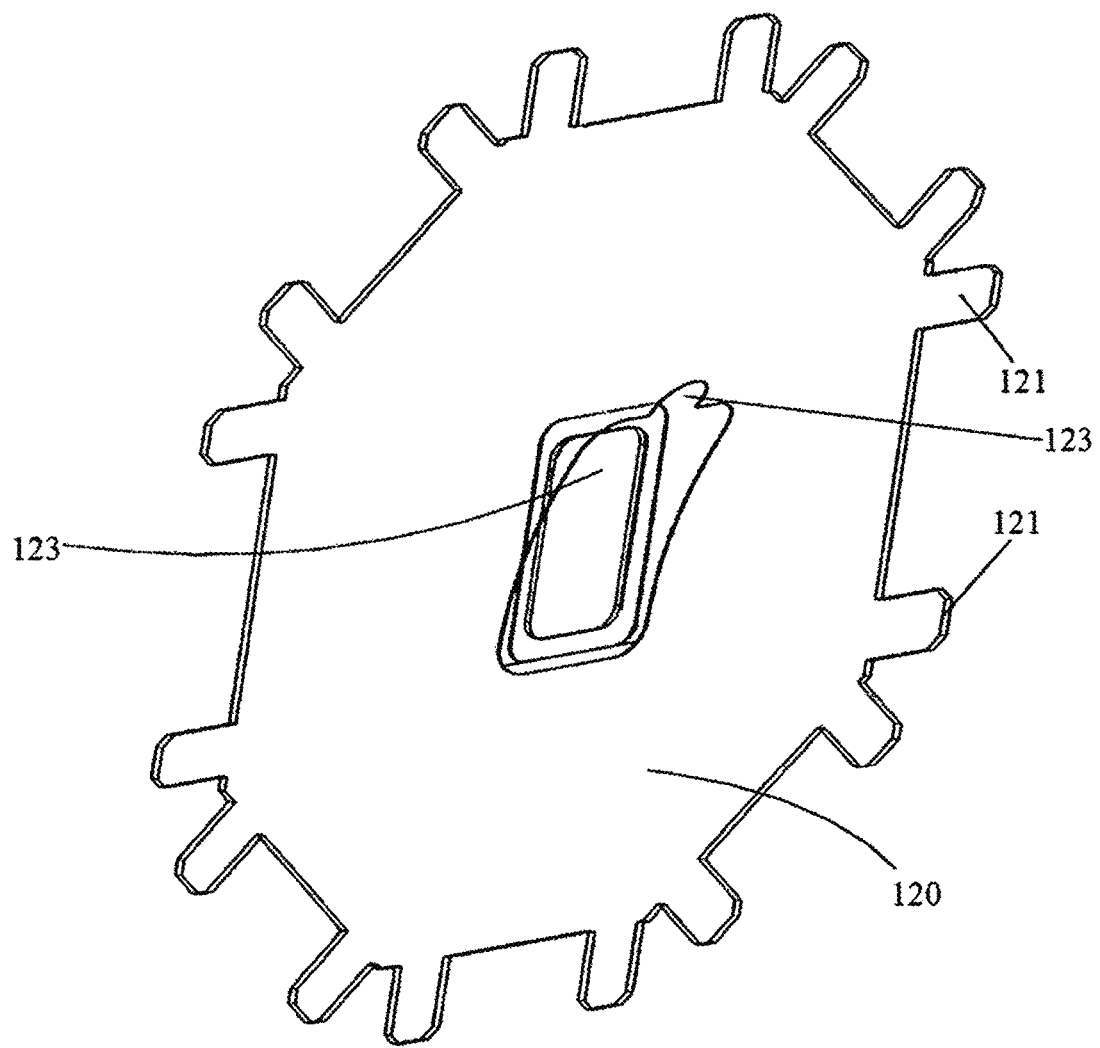
FIG. 4 is a bottom plan view of a protective layer comprising a removable flap.

FIG. 4 shows a bottom plan view of the protective layer 120 showing a plurality of peel-off tabs 121 distributed along the outer edges allowing easy removal of the protective layer 120 from the wound pad. The protective layer 120 may comprise a peel-off sticker configured to protect the bottom surface from external contaminants thereby maintaining the wound pad in a sterile condition. In an embodiment, the protective layer 120 further comprises the flap 123 which is removable prior to attachment of the veterinary adaptor during treatment of an animal with a penetrating wound. The flap 123 is removable independent of the protective layer 120.

Figure 5:
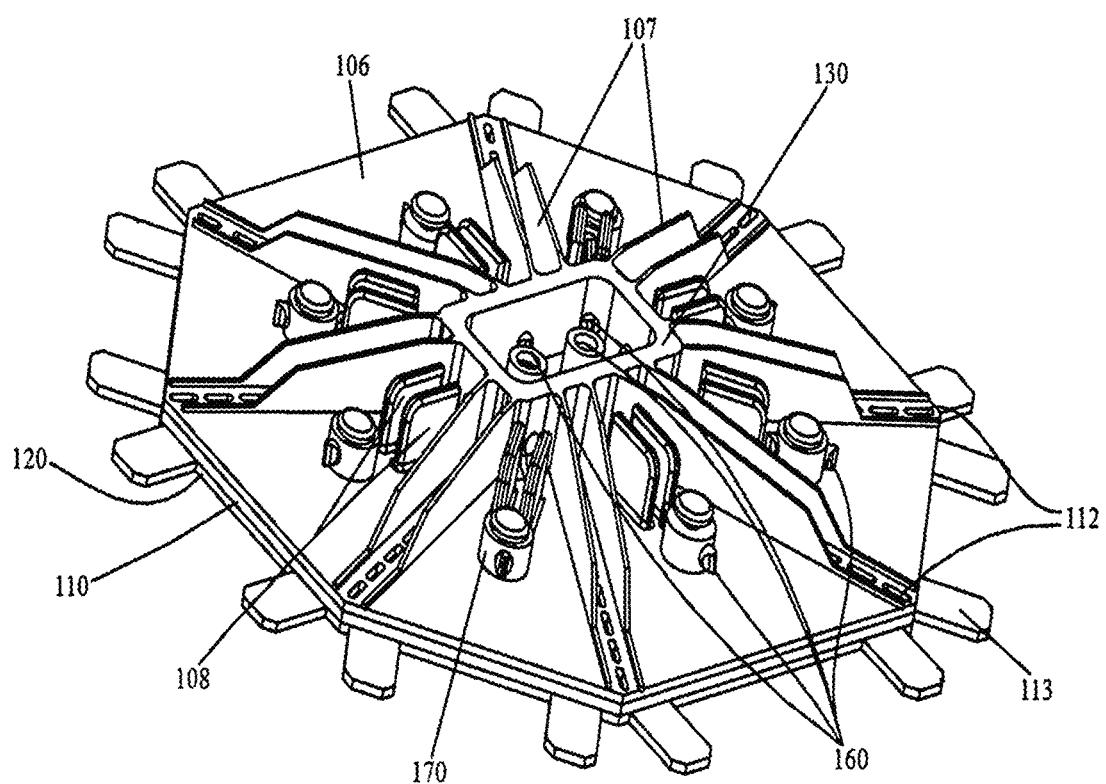
FIG. 5 is a top perspective view of the wound pad comprising a plurality of segments.

Referring to FIG. 5, the central vacuum column 130 is mounted over at least one unidirectional valve 160 which allows evacuation of air or fluid from the pleural cavity but prevents the return of air or fluid from the vacuum column 130 to the chest wall. The unidirectional valve 160 is a one-way pressure valve that allows exit of harmful air of fluid from the pleural cavity but prevents re-entry of air or fluid into the thoracic cavity. The plurality of segments 106 of the wound pad 110 are separated from each other by air tight walls 107. Each wound pad segment 106 comprises a plurality of ridge members 108 configured to support the vacuum dome. Each of the plurality of wound pad segments 106 comprises at least one opening sealed by at least one manually closable valve 170. The manually closable valve 170 in each segment 106 allows firm placement of different segments 106 over separate wounds by creating an airtight seal. One or more manually closable valves 170 of the wound pad segments 106 can be closed in an event when the body morphology of wounded victim requires the closure of one or more respective sealing units to prevent air from entering into the vacuum system. In an embodiment, each of the plurality of wound pad segments 106 comprises at least one opening sealable by a unidirectional valve 160, which allows evacuation of air and liquid from the pleural cavity of the victim with an open chest wound.

The perforated line 112 running between the air tight walls 107 of two adjacent wound pad segments 106 define the area of separation for each segment 106. In an embodiment, the wound pad segments 106 are separable from each other, whereas the inner edge of the segments 160 remains attached to the central vacuum column 130. For example, one or more wound pad segments 106 can be separated by tearing along the perforated lines 112, followed by lifting and folding the segment 106 upwards and adhering it to the base of the vacuum column 130 using the adhesive strip. The wound pad comprises at least one tear tab 113 for each segment 106, the tear tab 113 disposed along the edges of the wound pad 110 allows the segments 106 to be separated along the perforated lines 112. According to an exemplary embodiment, as shown in FIG. 5, the wound pad 110 comprises eight segments 106 forming eight different sectors configured to independently seal multiple open chest wounds. The protective layer 120 is configured to cover the bottom surface of the wound pad 110. In an embodiment, the unidirectional valve 160 comprises at least one atmospheric valve and a manually closable valve 170. Each of the plurality of wound pad segments 106 comprises at least one opening sealed by the manually closeable valve 170.

Figure 6:
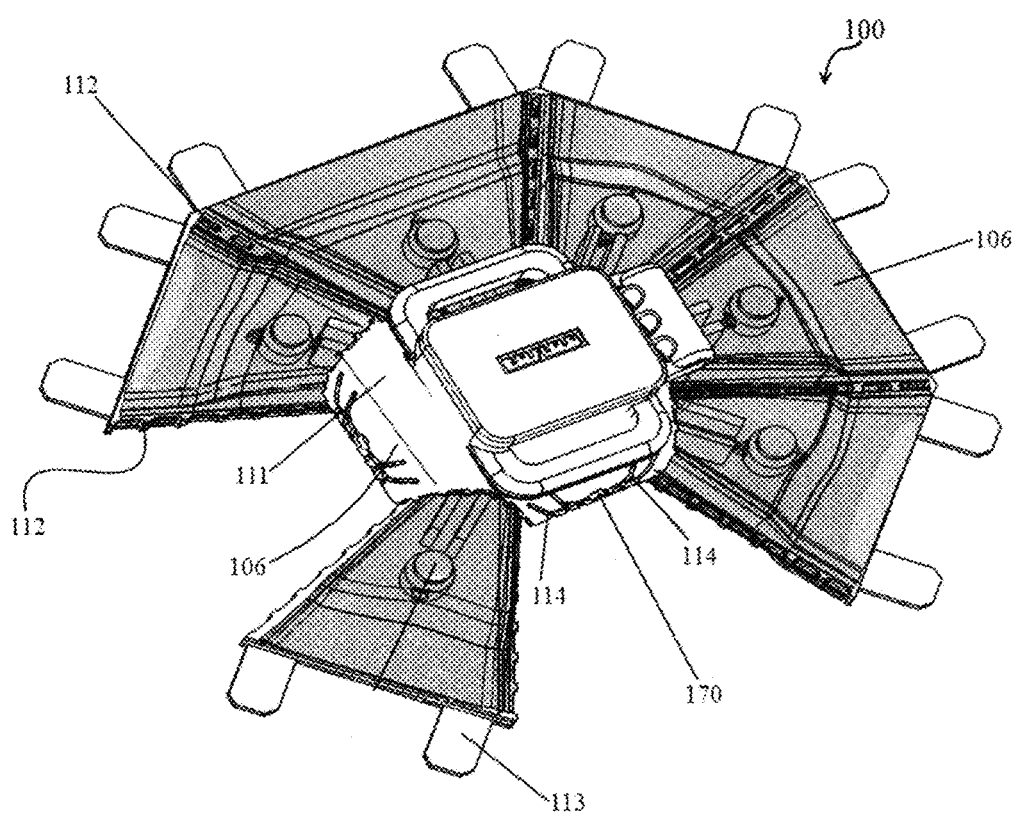
FIG. 6 is a top plan view of the wound pad with two segments folded out.
Figure 7:
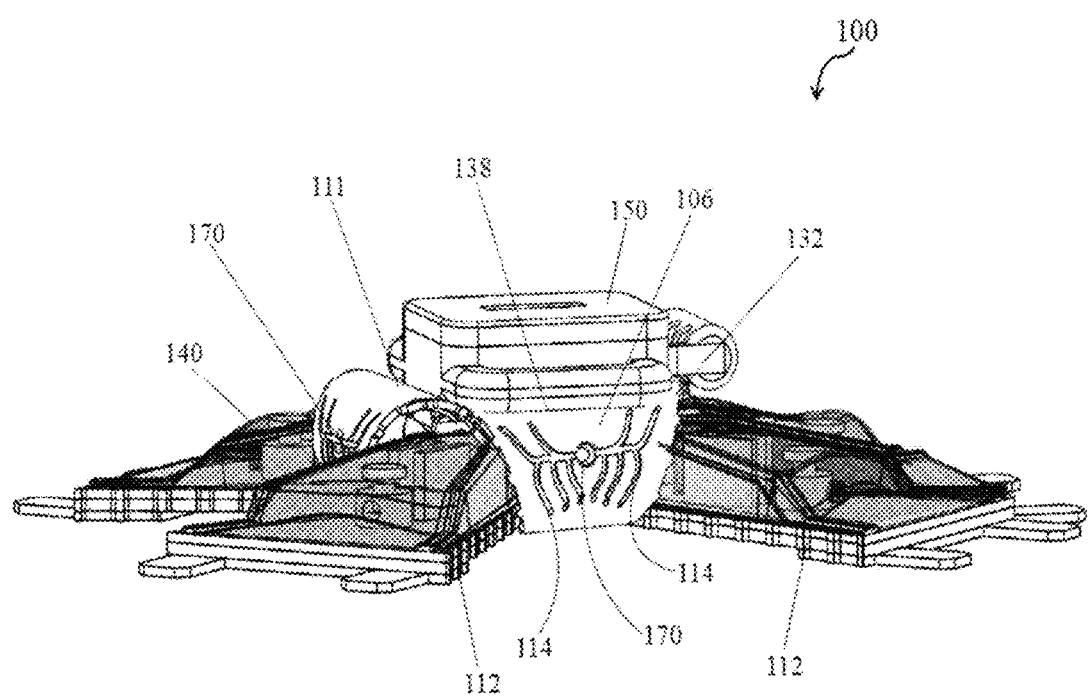
FIG. 7 is a side view of the wound pad with two segments folded out.

According to an exemplary embodiment, FIG. 6 and FIG. 7 illustrate different perspective views of the chest wound seal device 100 with two of the plurality of wound pad segments 106 folded out. One or more wound pad segments 106 can be folded out by holding the tear tab 113 of the respective segment 106 and by tearing along perforated lines 112 disposed on either side of the segment 106. The respective wound pad segment 106 can be lifted and folded out such that the adhesive strip 111 of the segment 106 adheres to the base of the vacuum pump 150, as shown in FIGS. 6 and 7. The bottom surface of the wound pad segment 106 shows a plurality of air channels 114 connected to at least one opening sealable by the manually closeable valve 170, the air channels 114 allow efficient movement of air from multiple wounds to the vacuum chamber. The vacuum dome 140 is disposed on the top surface of segments 106 of the wound pad 110. The chest wound seal device 100 further comprises the vacuum pump 150 operatively connected to the central vacuum column 130. The vacuum pump 150 is adapted to be attached to a vacuum pump seat 138 disposed within the central vacuum column 130. The vacuum pump seat 138 allows proper sealing of the vacuum pump 150 to the wound pad 110 as well as functions acts as a seat for the placement of vacuum dome 140. In an embodiment, the vacuum dome 140 is flexible and made of a transparent or semi-transparent material. In another embodiment, the vacuum dome 140 is further divided into a plurality of pie-shaped sectors disposed over each of the segments 106 of the wound pad 110, thus forming independent sealing units.

Figure 8:
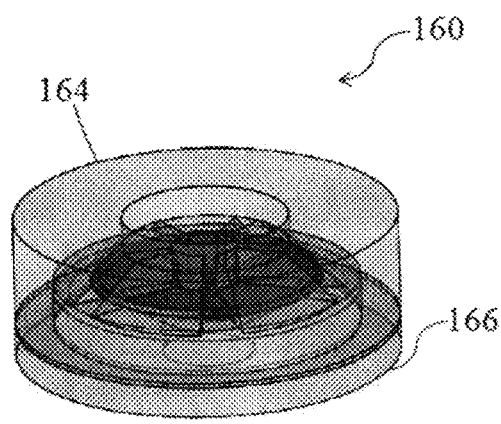
FIG. 8 is a perspective view of a unidirectional valve.
Figure 9:
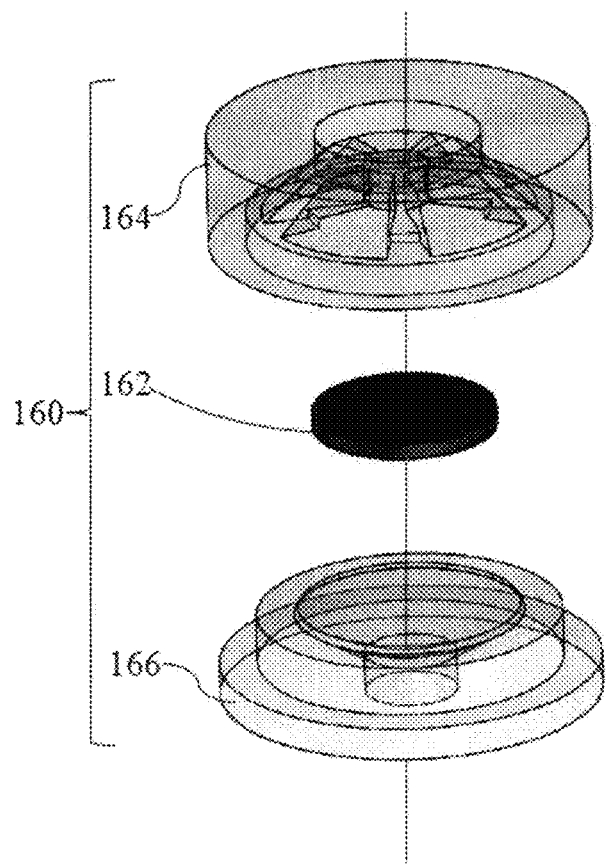
FIG. 9 is an exploded view of the unidirectional valve.

Referring to FIG. 8 and FIG. 9, the assembled and exploded views of the unidirectional valve 160 are illustrated respectively. The unidirectional valve 160 comprises a sealing disk 162 configured to vertically move within the valve body 164 due to pressure exerted by the entry of air or liquid from the chest cavity. The unidirectional valve 160 generally remains in a closed position due to the sealing disk 162 resting above a base 166 of the valve 160 as a response to atmospheric pressure thus preventing ingress of air or liquid. The unidirectional valve 160 opens as the sealing disk 162 moves upwards within the valve body 164 due to a differential pressure from the vacuum pump and the positive pressure from the harmful air or liquid in the chest cavity, thus allowing ingress of air and liquid from the chest cavity.

Figure 10:
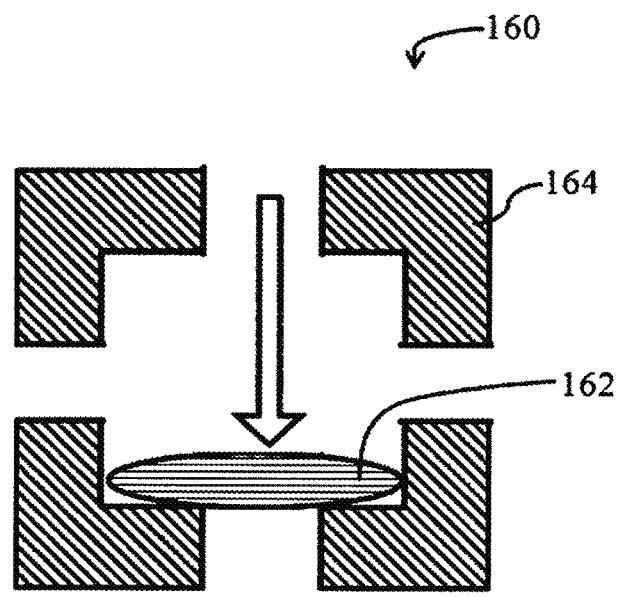
FIG. 10 is a sectional view of the unidirectional valve in a closed position.
Figure 11:
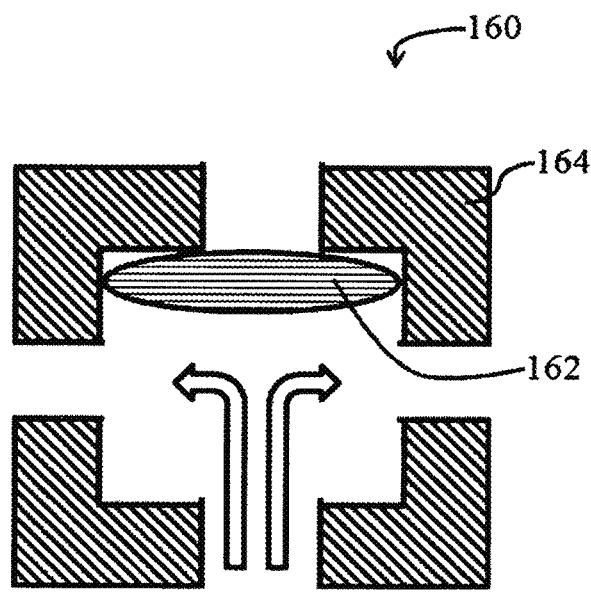
FIG. 11 is a sectional view of the unidirectional valve in an open position.
Figure 12A:
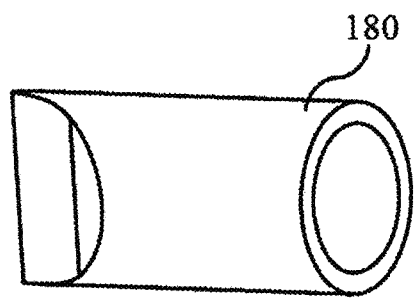
FIGS. 12A and 12B are views of air channel pathway.
Figure 12B:
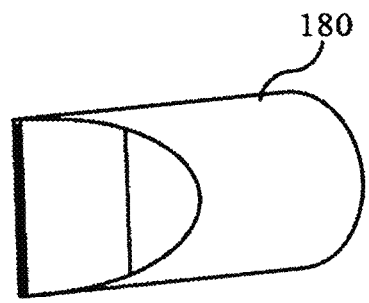

Referring to FIG. 10 and FIG. 11, which show sectional views of the unidirectional valve 160 in a closed and an open position respectively. In a closed position, the sealing disk 162 rests at the base of the valve body 164 responding to atmospheric pressure thus blocking any entry of air or liquid into the unidirectional valve 160. The movement of the sealing disk 162 within the unidirectional valve 160 is indicated by an arrow in FIG. 10. In an open position, air or liquid is allowed to enter through an orifice in the wound pad into the unidirectional valve 160 thus pushing up the sealing disk 162 for allowing the air or fluid to escape into the vacuum dome. The direction of flow of air and liquid through the valve 160 is indicated by thick arrows in FIG. 11. The sealing disk 162 is configured to move upwards within the valve body 164 due to the pressure exerted by the air or liquid exiting from the pleural cavity thus opening the unidirectional valve 160. The wound pad 110 further comprises air channel pathway 180 as shown in FIGS. 12A and 12B. The air channel pathway 180 is configured to ensure that the vacuum thus formed is maintained.

Figure 13:
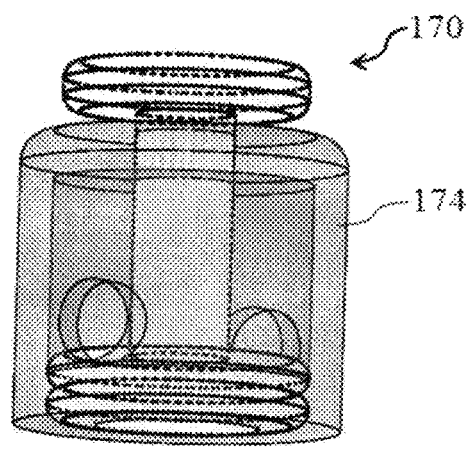
FIG. 13 is a side view of a manually closeable valve in a closed position.
Figure 14:
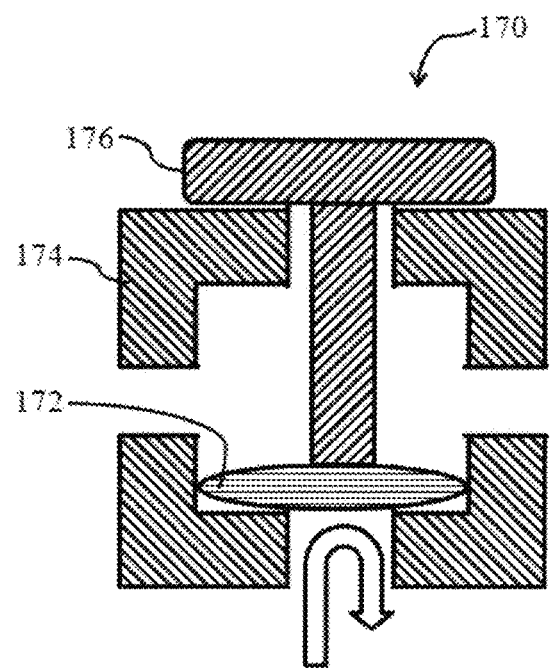
FIG. 14 is a sectional view of the manually closeable valve in the closed position.

Referring to FIGS. 13 and 14, side perspective and sectional views of the manually closeable valve in a closed position has been illustrated respectively. The manually closeable valve 170 comprises a sealing disk 172 configured to be moved within a valve body 174 by a valve closure actuator 176. In a closed position, a plurality of openings at the base of the valve 170 is sealed by the sealing disk 172 thus preventing air from entering from each sealing unit. One or more sealing units can be kept closed independently with the help of manually closeable valve 170 when those sealing units are not in use or when those sealing units are not functioning properly. In order to close the manually closeable valve 170, the valve closure actuator 176 is manually pushed down which in turn pushes the sealing disk 172 downwards to reach the base thus blocking the openings at the base of the valve body 174. The movement of the valve closure actuator 176 is configured to preclude its motion from being on the same axis as the angle of entry of the thoracic wound.

Figure 15:
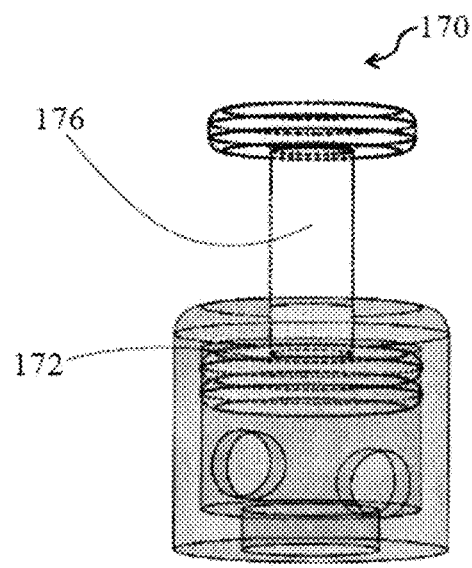
FIG. 15 is a side view of the manually closeable valve in an open position.
Figure 16:
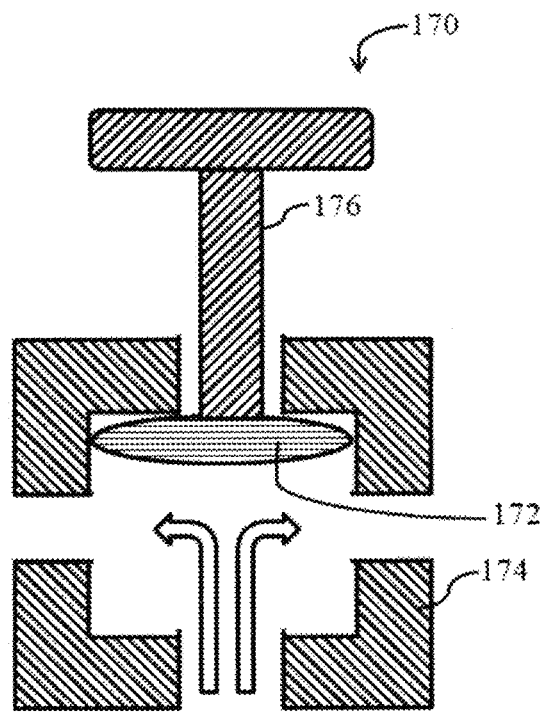
FIG. 16 is a sectional view of the manually closeable valve in open position.

Referring to FIGS. 15 and 16, side perspective and sectional views of the manually closeable valve 170 in a open position has been illustrated respectively. The valve closure actuator 176 is manually pulled upwards which in turn pulls the sealing disk 172 upwards toward the top of the valve body 174 in order to form a tight seal. One or more manually closable valves 170 disposed on the segments of wound pad can be used to create independent sealing units over multiple wounds. Manually closable valves 170 along with airtight walls of each wound pad segment allow the wound pad to be customized according to the wounded individual's body morphology. The manually closable valve 170 allows wound pad segments to be secured over separate wounds by providing an airtight seal against the skin surface of the wounded body. The manually closable valves 170 are configured to be closed in the event that the body morphology requires the closure of one or more valves 170 to prevent air from entering into the vacuum system.

Figure 17:
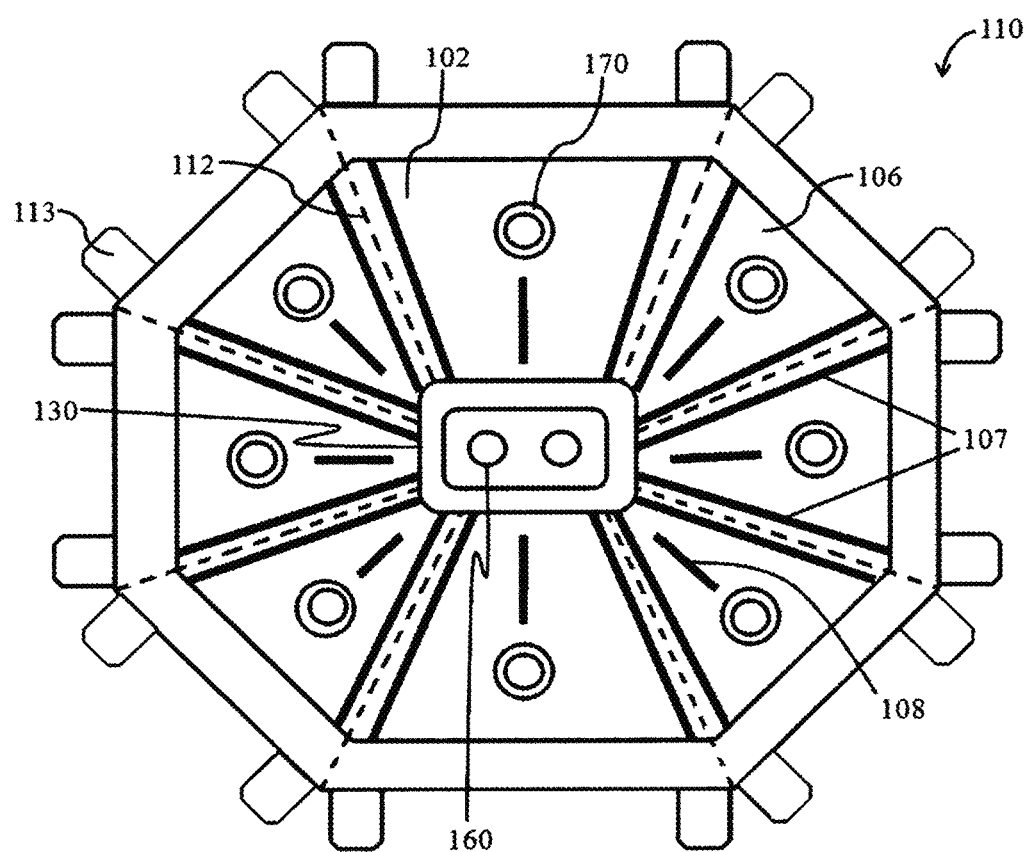
FIG. 17 is a top plan view of the wound pad with the plurality of segments radiating from central vacuum column.

Referring to FIG. 17, the wound pad 110 comprises the plurality of segments 106 radiating from the central vacuum column 130. The wound pad segments 106 are separated from each other by airtight walls 107 on the top surface 102. The wound pad 110 further shows perforated line 112 between the airtight walls 107 of two adjacent segments 106, the perforated line 112 allows separation of one or more of the plurality of wound pad segments 106. Each of the wound pad segments 106 comprise at least one manually closeable valve 170 for sealing each segment 106 and at least one ridge member 108 for supporting the vacuum dome adapted to be disposed above the wound pad 110. The central vacuum column 130 is mounted above at least one unidirectional valve 160. Each wound pad segment 106 comprises at least one tear tab 113 distributed along the circumferential edges of the wound pad 110.

Figure 18:
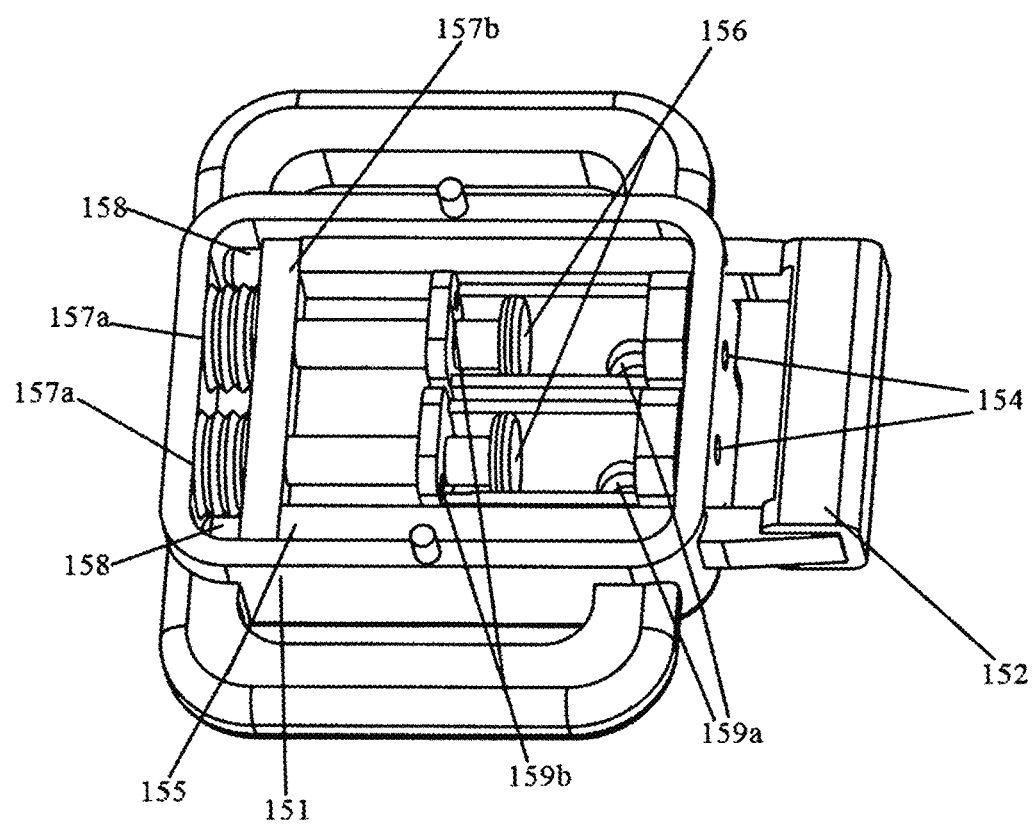
FIG. 18 is a top perspective view of the vacuum pump in a closed position.
Figure 19:
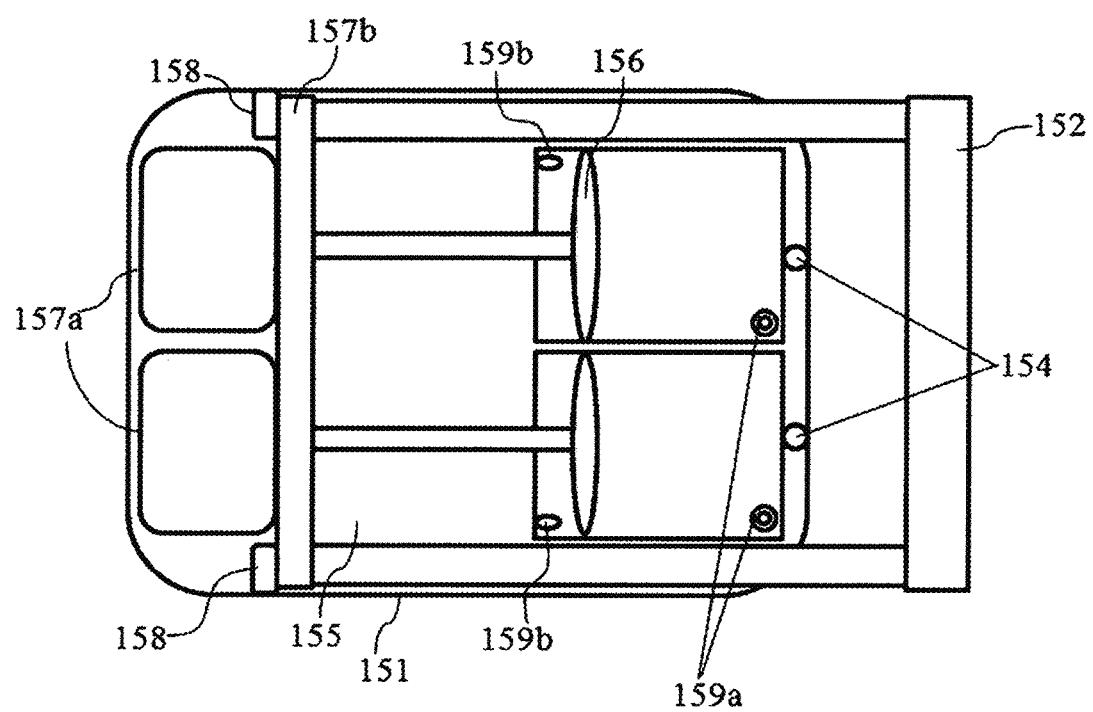
FIG. 19 is a schematic representation of the vacuum pump in the closed position.
Figure 20:
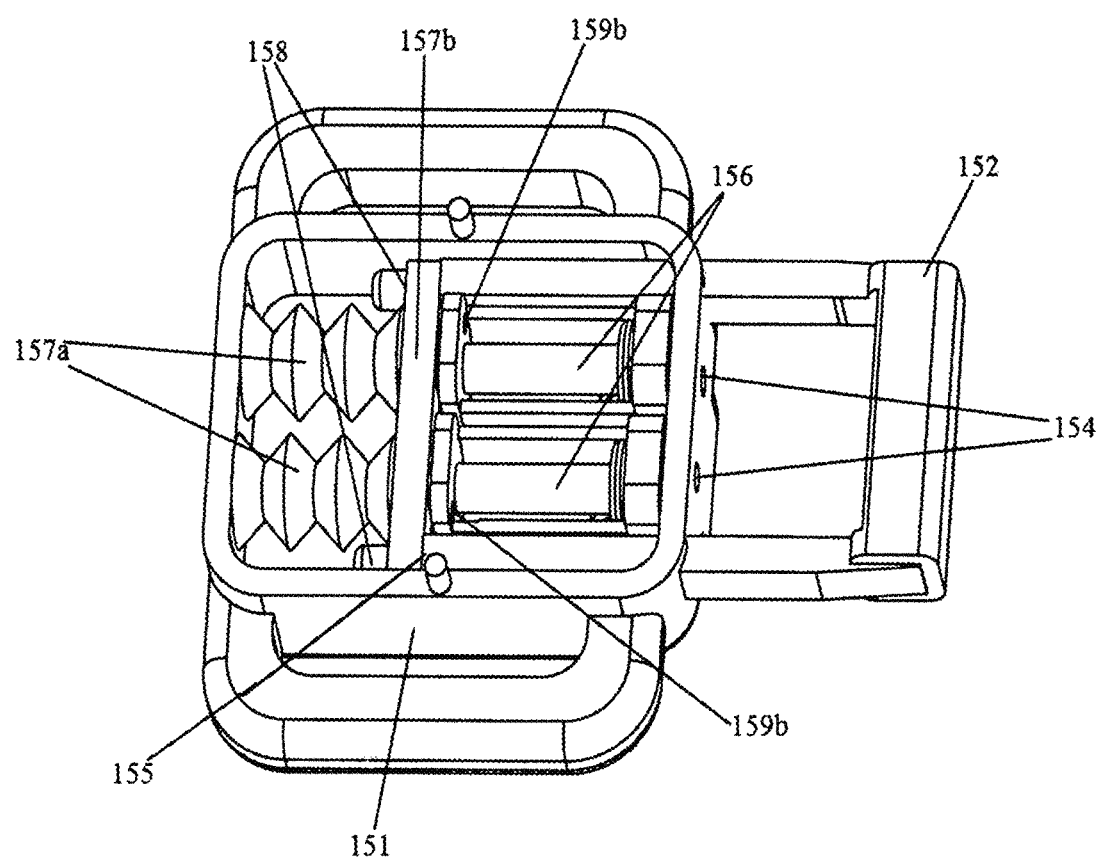
FIG. 20 is a top perspective view of the vacuum pump in an open position.
Figure 21:
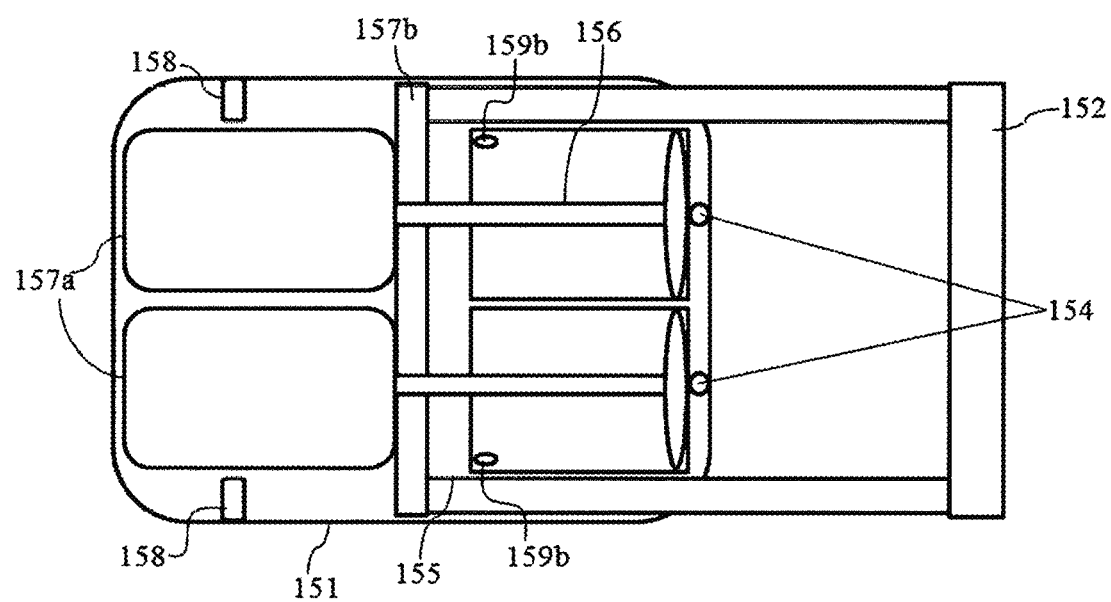
FIG. 21 is a schematic representation of the vacuum pump in the open position.

Referring to FIGS. 18 through 21, the vacuum pump 150 comprises a vacuum pump case 151 and a vacuum pump actuation handle 152. The vacuum pump 150 is adapted to be attached to a vacuum pump seat disposed within the vacuum column of wound pad, wherein the vacuum pump seat within the vacuum column allows proper sealing of the vacuum pump 150 to the wound pad as well as functions acts as a seat for the placement of flexible vacuum dome. FIGS. 18 and 19 illustrate different views of the vacuum pump 150 in a closed position. FIGS. 20 and 21 illustrate different views of the vacuum pump 150 in an open position. The vacuum pump 150 is configured to be easily actuated between closed and open positions by operating the actuation handle 152.

The vacuum pump case 151 comprises one or more expulsion outflow one-way valves 154, which allow for the ejection of air and fluid from the vacuum pump 150 when the vacuum pump 150 is in use. The vacuum pump 150 further comprises a vacuum chamber 155 in which a plunger and rod 156 moves to create an airtight seal creating a vacuum inside the chamber 155, thus drawing air and liquid from the vacuum column through at least one unidirectional valve. The air and liquid are drawn into the vacuum chamber 155 through vacuum intake one-way valves 159a. This vacuum is formed by the compression of the vacuum pump actuation handle 152 and the compression of a plurality of compression rubber springs 157a by a compression plate 157b against a base of the vacuum pump case 151. The air present on the opposing side of the plunger and rod 156 is evacuated freely through an air escape orifice 159b thus preventing further compression within the vacuum chamber 155 behind the plunger and rod 156. The stop blocks 158 at the base of the actuation handle 152 limits the range of motion of vacuum pump actuation handle 152 prior to the movement of the plunger and rod 156 by allowing the air to reach the air escape orifice 159b.

Figure 22:
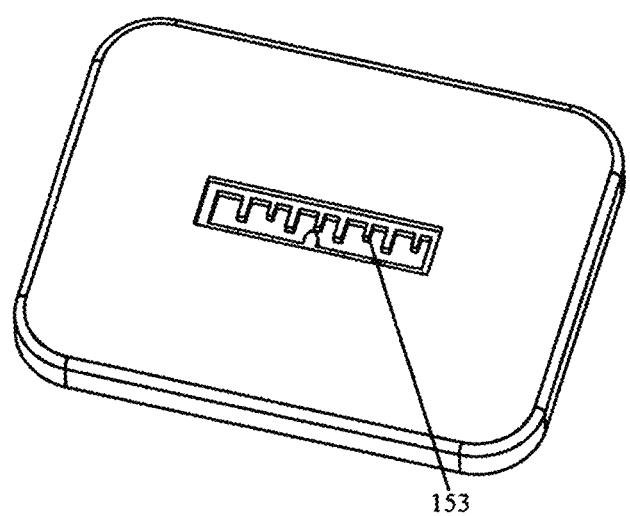
FIG. 22 is a top perspective view of the vacuum gauge.

Upon the completion of the vacuum producing stroke, pressure is manually released from the vacuum pump actuation handle 152 allowing the compression rubber springs 157a to return the vacuum pump actuation handle 152 and the plunger and rod 156 by pushing the compression plate 157b to its original position. This action is called the expulsion phase in which air and liquid are expelled from the device through the expulsion outflow one-way valves 154. The vacuum pump 150 further comprises a vacuum gauge 153 as shown in FIG. 22. The function of the vacuum gauge 153 is to determine the relative effectiveness of both the vacuum pumping action and effectiveness of the seal once proper air evacuation begins.

Figure 23:
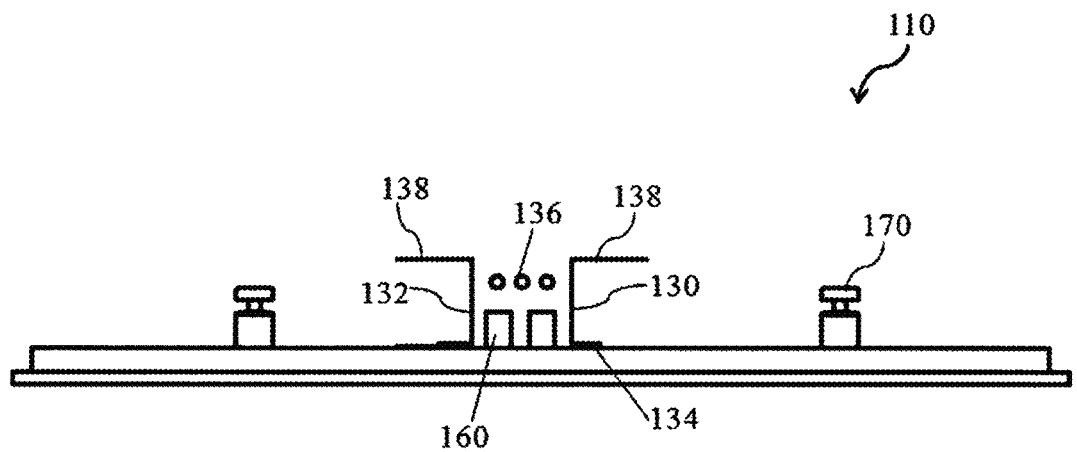
FIG. 23 is a sectional view of the central vacuum column mounted on the wound pad.

Referring to FIG. 23, a sectional view of the central vacuum column 130 mounted on the wound pad 110 has been illustrated. The central vacuum column 130 was mounted over at least one unidirectional valve 160, and each segment 106 of the wound pad 110 comprises at least one manually closeable valve 170. The central vacuum column 130 comprises a column wall 132 and a column base 134 sealed to the central portion on top surface of the wound pad 110. The column wall 132 contains a plurality of openings 136 to allow the differential air pressure from the vacuum pump to be transferred from the vacuum dome through the central vacuum column 130. The central vacuum column 130 comprises the vacuum pump seat 138 formed on top of the column wall 132 which allows for the positioning of the vacuum pump and also acts as a seat for the flexible vacuum dome.

Again referring to FIG. 1 and FIG. 5, the chest wound seal device 100 of the invention comprising the wound pad 110 with segments 106 and closable valves 160, 170 allows effective sealing of open chest wounds, evacuation of harmful air from the pleural cavity and prevention of atmospheric air re-entering the wound, thus making it possible to re-inflate the collapsed lung of the wounded victim. Evacuation of harmful air and liquid from the pleural cavity allow expansion of the ribs to create a vacuum necessary to restore proper lung function. In the event of exit wounds or additional wounds that have penetrated the pleura, each wound can be individually closed by forming independent airtight seals using the plurality of segments 106 of the wound pad 110, which allows re-inflation of the collapsed lung. The unidirectional valve 160 control flow of air and fluid from higher pressure areas in the wound to low-pressure areas created by the vacuum pump 150, before expelling the air and the fluids.

The Unisex Multi-Morphology Traumatic Pneumothorax Chest Seal and Vacuum Pump device 100 of the present invention can also be adapted for veterinary applications. For example, when an animal is being shot or impaled by an arrow, which is a frequent occurrence during hunting accidents or when animals are frightened, they tend to impale themselves on fence posts or similar sharp penetrating objects forming penetrating wounds. The Unisex Multi-Morphology Traumatic Pneumothorax Chest Seal and Vacuum Pump device 100 can be adapted to provide appropriate first treatment to injured animals with penetrating thoracic wounds by sealing the wound appropriately and providing relief from a collapsed lung.

Figure 24:
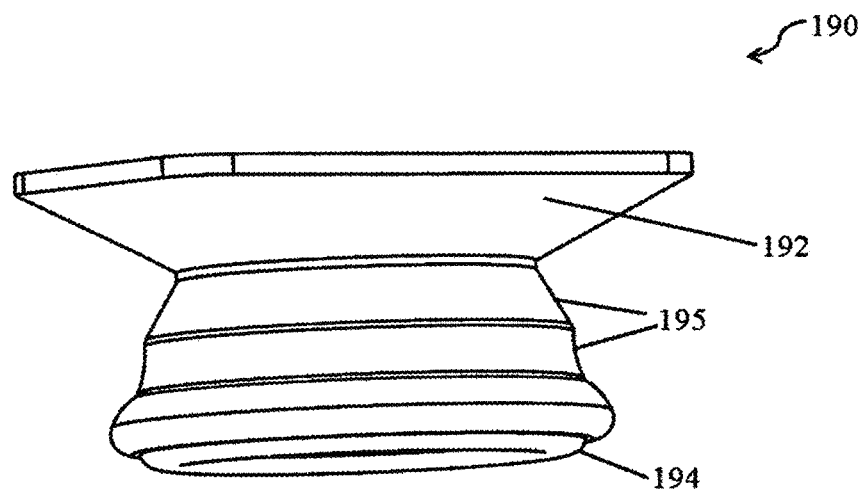
FIG. 24 is a side view of a veterinary adaptor mount.
Figure 25:
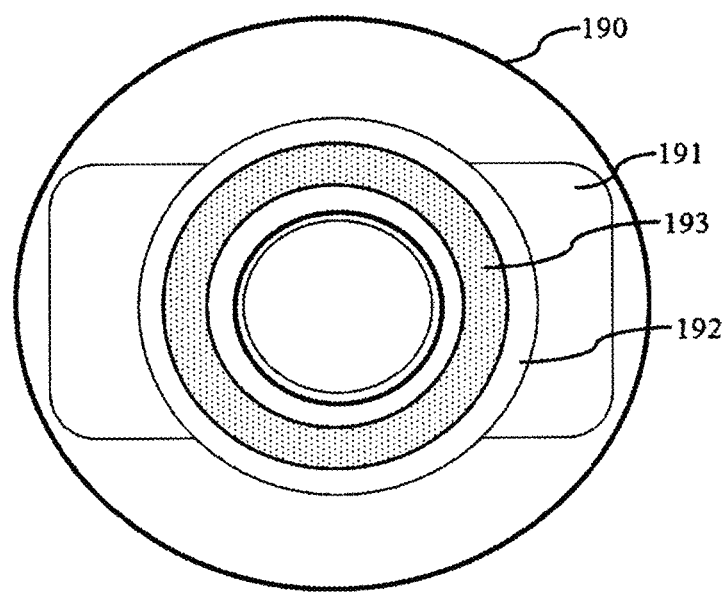
FIG. 25 is a bottom plan view of the veterinary adaptor mount.

Referring to FIGS. 24 through 27, a veterinary adaptor 190 and a strap 196 with a buckle assembly 198 is illustrated. FIGS. 24 and 25 illustrate side perspective and bottom plan views of the veterinary adaptor 190 respectively. The veterinary adaptor 190 comprises an adaptor mouth 192 and a plurality of compression bellows 195 situated above a wound contact ring 194. The wound contact ring 194 comprises an adhesive jelly 193 covered by veterinary adaptor protection flap 191. The veterinary adaptor 190 is configured to be attached to the wound absorption pad after removal of the veterinary adaptor protection flap 191.

Figure 26:
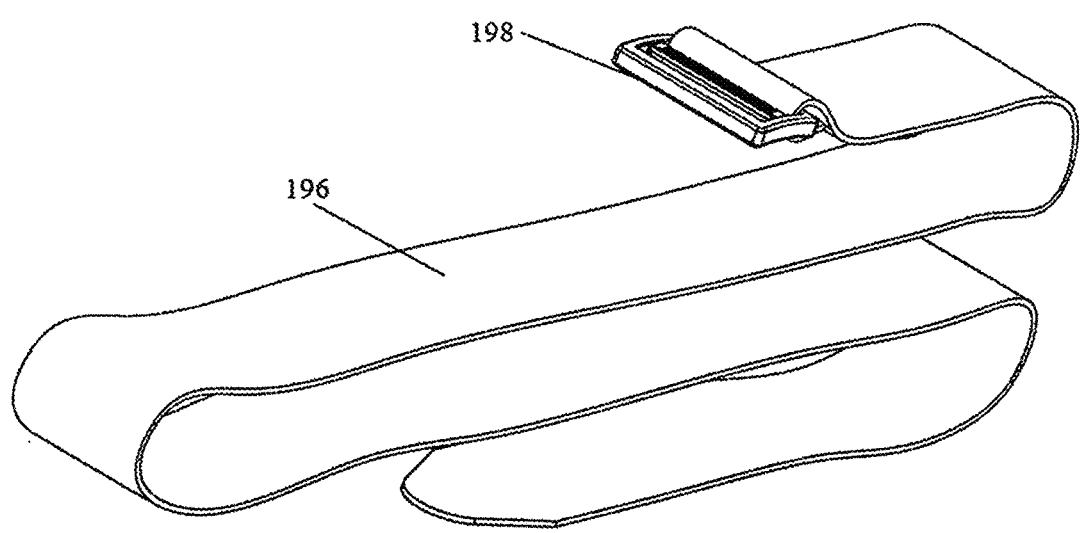
FIG. 26 is a perspective view of a hook and loop strap with a buckle system.

FIG. 26 illustrates the strap 196 and buckle assembly 198, which can be used for wrapping the chest wound seal device 100 around the wounded animal. In an embodiment, the strap 196 comprises a hook and loop type strap. The chest wound seal device 100 of the invention is configured to be used for treating a wounded animal by wrapping the hook and loop strap 196 around the wounded animal and securing using the buckle assembly 198 to adjust the overall tightness of the device 100.

Figure 27:
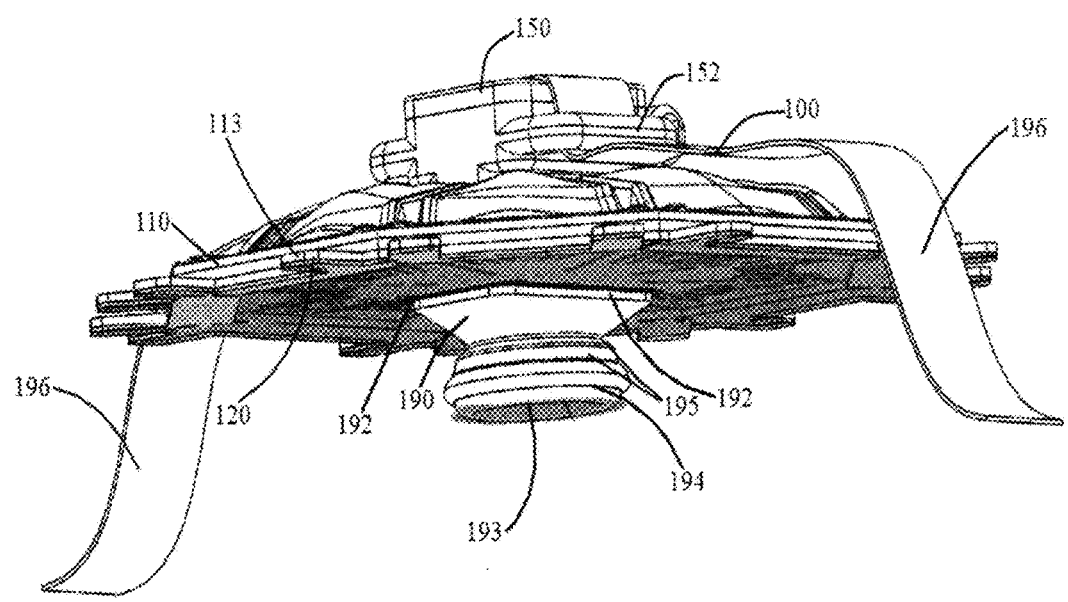
FIG. 27 is a perspective view of the wound pad attached to the adaptor mount and the strap and buckle system.

FIG. 27 illustrates chest wound seal device 100 attached with the veterinary adaptor 190 and the hook and loop strap 196. By attaching a mouth 192 of the adaptor 190 to the adhesive present on the wound pad 110 and securing with the hook and loop strapping 196, the device 100 can be easily adapted for use on a wide variety of different sized animals with penetrating thoracic wounds. For example, an animal care provider can remove the veterinary adaptor protection flap 191 thus exposing the sterile adhesive jelly 193 contained within a wound contact ring 194 and place the adaptor 190 over the wound. The expansion of the sterile adhesive jelly 193 around a wound creates an air-tight seal between the adaptor 190 and skin surface of the animal; the adhesive jelly 193 is capable of forming an airtight seal even on a hair covered animal skin surface. The compression bellows 195 should be at their maximum extension before securing the strapping system 196.

The top surface of the wound pad 110 is attached to the vacuum pump 150. Once the device 100 is secured over the wound of the injured animal, repeated compressions of the actuation handle 152 of the vacuum pump 150 will provide a vacuum as indicated by the relative vacuum gauge disposed on top of the vacuum pump 150, thus allowing re-inflation of the collapsed lung. The compression bellows 195 are specifically designed to expand and compress with breathing of the wounded animal. A secondary sealing unit can be placed upon an exit wound if necessary.

The Unisex Multi-Morphology Traumatic Pneumothorax Chest Seal and Vacuum Pump device 100 of the invention solves multiple problems that are not addressed by the prior art devices. Primarily, the device 100 can be used to treat wounded victims with different body types and morphology, by selectively folding out one or more sectors 106 of the wound pad 110 while still maintaining an air tight seal against the skin. The wound pad 110 when attached to a body of a wounded victim, is configured to cover the wounded region by the plurality of segments 106 radiating from the central vacuum column 130. Shock acts as a significant contributing factor in the mortality of penetrating chest wounds. The device 100 allows either the injured subject or a first responder to reduce the chance of shock by rapidly beginning with the process of relieving pneumothorax, for example, the device 100 can be used to relieve a pneumothorax within 90 seconds. The device 100 also changes the direction of the force that needs to be applied by vacuum pump 150 thus decreasing the pain threshold of the injured person significantly. In a different embodiment, the device 100 further comprises a flexible extension tube and a strap to secure the wound pad to the body of the victim. While using the flexible extension tube, all of the wound pad segments 106 are folded up and the adhesive strip 111 of the segments 106 are made to adhere to the base of the vacuum pump 150.

In another embodiment, the invention relates to a method for treating a thoracic wound. The method comprising the steps of: i) securing a wound pad 110 to a victim's skin to cover a wound in a thorax of a victim, wherein the wound pad 110 comprises: a) at least one unidirectional valve 160 embedded in the covering pad 110 to enable evacuation of air from a pleural cavity and to prevent the air from re-entering the thorax; b) a vacuum column 130 mounted directly over at least one unidirectional valve 160; c) a plurality of wound pad segments 106 radiating from the vacuum column 130, wherein each of the plurality of segments 106 are separated by a perforated line 112 on the wound pad 110 between airtight walls 107 to form independently sealed areas; ii) connecting a vacuum pump 150 to the wound pad 110 through the vacuum column 130 to form an airtight seal, wherein the vacuum pump 150 comprises a handle 152; and iii) compressing the handle 152 to apply force in a direction normal to the wound to create vacuum, wherein the vacuum so created expels fluids from a pleural cavity of the victim.

According to the method, securing comprises attaching the wound pad 110 to the body by an adhesive layer 111. In an embodiment, the adhesive layer 111 is made of a biocompatible material. The securing comprises sealing at least one opening in the wound pad 110. The sealing comprises depressing an actuator 170 associated with each of the plurality of wound pad segments 106 and applying of force by depressing the actuator 170 creates a low-pressure area to draw the air from the pleural cavity.

One of the distinguishing features of the device 100 is its ability to be segmented while still providing a vacuum seal. No other device has this capacity, and no other device can approach the range of flexibility of this device 100 which can be utilized in different scenarios. The Unisex Multi-Morphology Traumatic Pneumothorax Chest Seal and Vacuum Pump device 100 of the present invention has a unique vacuum system that changes completely the scenario of pain management. The device 100 can be easily adapted to a veterinary scenario, where the survival rate of wounded animal could be doubled if this device was kept handy by the ranch, farm and rural pet owners who live adjacent to hunting regions.

The device 100 of the present invention possess numerous advantages over prior art. Some of the advantages of the chest wound seal device 100 include: 1. The ability of the device 100 to cover larger surface area allows sealing multiple penetrating chest wounds, for example, to seal multiple wounds resulting from a shotgun blast. 2) Wound pad 110 with segmented 106 design allows for customization of the wound pad 110 to adapt to wounded victims with different body types and morphological features due to gender, age, and body shape. 3) Provision to shut off one or more wound pad segments 106 by the use of manually closable valves 160, 170, when the segments 106 of the wound pad 110 are not in use or when the segments 106 are not functioning properly. 4) The wound pad design allows folding out one or more segments 106 of the wound pad 110 for a better fit to different types of bodies with a diverse range of morphological features. 5) Easily deployable active vacuum pump system 150 allows for first responders to immediately provide relief from a traumatic pneumothorax. 6) The device 100 is adaptable for both human and veterinarian use. 7) The vacuum pumping action does not require excess pressure being applied to the wound but works at a 90-degree angle allowing for greater patient comfort. 9) Relative vacuum gauge 153 allows to determinate the effectiveness of the vacuum pump 150 and exposes any failure in the seal. 10) Multiple vacuum chambers in the vacuum pump 150 compensate for fluid blockage or high viscosity fluids to be expelled. 11) The ergonomically designed vacuum pump 150 allows for one handed and continued operation. 12) The vacuum pump 150 can be felt and operated by using tactile sensation without any need for any external lighting thus making the device 100 suitable for operation in the dark. 13) The vacuum pump 150 integrated with the chest seal device 100 requires only a less range of motion for actuation.

The present invention has been described with a preferred embodiment thereof and it is to be understood that the invention is not to be limited to the disclosed embodiment, but on the contrary, many changes and modifications to the described embodiment can be carried out without departing from the scope and the spirit of the invention that is intended to be limited only by the appended claims.

What is claimed is:

1. A chest seal comprising a wound pad for sealing a penetrating thoracic wound, the wound pad comprising:
    a top surface comprising a nonporous layer and a bottom surface comprising a porous absorbent layer, wherein the porous absorbent layer comprises a plurality of air channels configured to evacuate air from multiple thoracic wounds;
    a plurality of unidirectional valves embedded on the top surface to enable evacuation of air from a pleural cavity and to prevent the air from re-entering the thorax;
    a central vacuum column mounted directly over at least one of the unidirectional valves, wherein the central vacuum column is adapted to be connected to a vacuum pump;
    a plurality of wound pad segments radiating from the central vacuum column, wherein the plurality of wound pad segments are separated from each other by a perforated line between airtight walls forming independent sealing areas,
    wherein the wound pad, when attached to a body of a victim, is configured to cover the wound by the plurality of segments radiating from the vacuum column, wherein one or more of the plurality of segments are configured to be folded out to suit the body of the victim,
    wherein the vacuum pump when connected to the wound pad through the vacuum column, creates a vacuum to draw air from the pleural cavity, wherein the vacuum pump enables application of normal force to the wound; and
    a flexible extension tube and a strap to secure the wound pad to the body of the victim.

2. The wound pad as claimed in claim 1 further comprises a cover disposed on the bottom surface of the wound pad to protect the wound pad from contaminants.

3. The wound pad as claimed in claim 2 further comprises an adhesive layer applied on the cover to hermetically seal the wound pad to the body of the victim.

4. The wound pad as claimed in claim 1, wherein each of the plurality of wound pad segments comprises at least one opening sealable by a manually closable valve.

5. The wound pad as claimed in claim 1, wherein the plurality of unidirectional valves comprises at least one atmospheric valve and a manual valve.

6. A thoracic wound sealing device comprising:
    a wound pad adapted to cover a wound in a thorax of a victim, the wound pad comprising:
        at least one unidirectional valve embedded in the wound pad to enable evacuation of air from a pleural cavity and prevent the air from re-entering the thorax;
        a vacuum column mounted directly over the at least one unidirectional valve;
        a plurality of wound pad segments radiating from the vacuum column, wherein the plurality of wound pad segments are separated by perforations between airtight walls to form separate sealed areas; and
    a vacuum pump connected to the wound pad through the vacuum column, the vacuum pump creates a vacuum to draw air from the pleural cavity, wherein the vacuum pump enables application of normal force to the wound.

7. The thoracic wound sealing device as claimed in claim 6 further comprises a cover disposed on a bottom surface of the wound pad to protect the wound pad from contaminants.

8. The thoracic wound sealing device as claimed in claim 6 further comprises an adhesive strip applied along edges of a bottom surface of the wound pad to hermetically seal the wound pad to a body of the victim.

9. The thoracic wound sealing device as claimed in claim 8, wherein the adhesive strip comprises a non-toxic elastomer.

10. The thoracic wound sealing device as claimed in claim 6, wherein each of the plurality of wound pad segments comprises at least one opening sealable by a manual valve.

11. The thoracic wound sealing device as claimed in claim 10, wherein the manual valve is closable by a movement of an actuator, wherein the movement of the actuator is so configured as to preclude its motions from being on the same axis as the angle of entry of the thoracic wound.

12. The thoracic wound sealing device as claimed in claim 6, wherein the at least one unidirectional valve controls flow of air and fluid from higher pressure areas in the wound to low-pressure areas created by the vacuum pump, before expelling the air and the fluid.

13. The thoracic wound sealing device as claimed in claim 6, wherein the vacuum pump is configured to form an air-tight connection with the vacuum column.

14. The thoracic wound sealing device as claimed in claim 6 further comprises:
    an extension tube connected to the wound pad in a direction opposite to the vacuum column; and
    a strap connected to the extension tube to enable securing of the device to the victim's body.

15. A method for treating a thoracic wound, the method comprising:
    securing a wound pad to a victim's body to cover a wound in a thorax of a victim, wherein the wound pad comprises:
        at least one unidirectional valve embedded in an upper surface of the wound pad to enable evacuation of air from a pleural cavity and prevent the air from re-entering the thorax;
        a vacuum column mounted directly over the at east one unidirectional valve; and
        a plurality of wound pad segments radiating from the vacuum column, wherein each of the plurality of segments are separated by perforations on the wound pad between airtight walls to form independently sealed areas;
    connecting a vacuum pump to the wound pad through the vacuum column to form an airtight seal, wherein the vacuum pump comprises a handle; and
    compressing the handle to apply force in a direction normal to the wound to create a vacuum, wherein the vacuum so created expels fluids from the pleural cavity.

16. The method as claimed in claim 15, wherein the securing comprises attaching the wound pad to the victim's body by an adhesive layer disposed on the bottom surface of the wound pad.

17. The method as claimed in claim 16, wherein the adhesive layer is biocompatible.

18. The method as claimed in claim 15, wherein the securing comprises sealing at least one opening in the wound pad.

19. The method as claimed in claim 18, wherein the sealing comprises depressing a closure actuator of a manually closeable valve associated with each of the plurality of wound pad segments.

20. The method as claimed in claim 15, wherein the applying of force creates a low-pressure area to draw the air from the pleural cavity.

* * * * *